(12) United States Patent
Tello

(10) Patent No.: US 11,628,189 B2
(45) Date of Patent: Apr. 18, 2023

(54) AMNIOTIC OR PLACENTAL DEVICE FOR OPHTHALMIC USE AS A DRESSING WITH REFRACTORY CENTER SECTION

(71) Applicant: Celso Tello, Rye, NY (US)

(72) Inventor: Celso Tello, Rye, NY (US)

(\*) Notice: Subject to any disclaimer, the term of this patent is extended or adjusted under 35 U.S.C. 154(b) by 477 days.

(21) Appl. No.: 16/785,796

(22) PCT Filed: Aug. 7, 2018

(86) PCT No.: PCT/US2018/045530
§ 371 (c)(1),
(2) Date: Feb. 10, 2020

(87) PCT Pub. No.: WO2019/094073
PCT Pub. Date: May 16, 2019

(65) Prior Publication Data
US 2020/0215121 A1    Jul. 9, 2020

Related U.S. Application Data

(60) Provisional application No. 62/544,770, filed on Aug. 11, 2017.

(51) Int. Cl.
*A61F 9/00* (2006.01)
*A61K 35/50* (2015.01)
*A61L 27/36* (2006.01)
*A61L 27/52* (2006.01)
*A61L 27/54* (2006.01)
*A61L 27/58* (2006.01)

(52) U.S. Cl.
CPC ............ *A61K 35/50* (2013.01); *A61F 9/0017* (2013.01); *A61L 27/3604* (2013.01); *A61L 27/52* (2013.01); *A61L 27/54* (2013.01); *A61L 27/58* (2013.01)

(58) Field of Classification Search
CPC ...................................................... A61F 9/0017
See application file for complete search history.

(56) References Cited

U.S. PATENT DOCUMENTS

2016/0220485 A1\* 8/2016 Tello ....................... A61L 27/58

\* cited by examiner

*Primary Examiner* — Benjamin J Packard
(74) *Attorney, Agent, or Firm* — Andrew Berks; Gallet Dreyer & Berkey LLP

(57) ABSTRACT

A biodegradable lens-shaped patch useful for healing and treatment of ocular conditions is disclosed. The patch is formed from a biodegradable carrier which carries amniotic extract and/or placental extract. The lens-shaped patch may be shaped in the form of a conventional contact lens and it is applied to a corneal surface to enhance healing thereof. After a certain period of time, the patch dissolves on its own and it need not be removed from the eye by a clinician. In an embodiment, the patch includes a clear central section that may be refractory, and a biodegradable peripheral section.

6 Claims, 4 Drawing Sheets

AMNIOTIC OR PLACENTAL DEVICE FOR OPHTHALMIC USE AS A DRESSING WITH REFRACTORY CENTER SECTION

CROSS REFERENCE TO RELATED APPLICATIONS

This patent application is a United States National Phase Entry under 35 USC § 371 of PCT International patent application PCT/US2018/045530, filed Aug. 7, 2018, and claiming priority to U.S. Patent Provisional Application 62/544,770, filed Aug. 11, 2017.

FIELD OF THE INVENTION

This invention pertains to a patch and lens for ocular use, wherein the patch comprises an amniotic or placental extract in a resorbable layer, and wherein the patch includes a clear central portion that may be refractory.

BACKGROUND OF THE INTENTION

Treatment of ocular surface disorders requires medical and surgical intervention, both acutely and in the long term. Regardless of the underlying causes involved, the common goals of management include controlling inflammation and promoting ocular surface healing with maximal visual rehabilitation. Various medical therapies have been used to achieve these objectives.

Amniotic membrane (AM) graft has been used in ophthalmology for several indications because of its beneficial effects. Amniotic compositions, such as amniotic membrane and extracts from amniotic membrane obtained from amniotic tissue derived from mammals, such as humans, pigs, or horses, include biological growth factors. Amniotic membrane is a biological membrane that lines the inner surface of the amniotic cavity and comprises a simple, cuboidal epithelium, a thick basement membrane, and an avascular mesenchymal layer containing hyaluronic acid. Amniotic compositions are known to reduce inflammation, fibrovascular ingrowth, and to facilitate epithelialization in animal models. Amniotic membrane is believed to play a role in the scarless wound healing process in a fetus.[1]

[1] U.S. Pat. No. 7,494,802; Tseng, S.-C.-G., et al., "Suppression of Transforming Growth Factor-Beta Isoforms, TGF-β Receptor Type II, and Myofibroblast Differentiation in Cultured Human Corneal and Limbal Fibroblasts by Amniotic Membrane Matrix," *J. Cell. Physiol.*, 179: 325-335 (1999).

Previous studies revealed that early intervention with amniotic membrane transplantation (AMT results in marked reduction of inflammation, rapid restoration of the ocular surface, and improved visual acuities while preventing cicatricial complications.[2] However, surgically performed AMT renders a relatively high cost and potentially unnecessary surgical trauma in such compromised eyes. Furthermore, the membrane patch usually dissolves within several days so that multiple sessions of AMT may be required. Previously, a self-retaining AM mounted on a double ring system has been effectively used to promote healing and reduce corneal scarring in a variety of ocular surface disorders,[3] however, patients experienced ocular discomfort from the ring and incomplete healing.[4]

[2] Dua H S, Gomes J A, King A J, et al. The amniotic membrane in ophthalmology. *Surv Ophthalmol*. 2004; 49:51-77.
[3] Pachigolta G, Prasher P, Di Pascuale M A, McCulley J P, McHenry J O, Mootha V V. Evaluation of the role of ProKera in the management of ocular surface and orbital disorders. *Eye Contact Lens*. 2009; 35:172-175.
[4] Surl K, Kosker M, Raber I M, et al. Sutureless Amniotic Membrane ProKera for Ocular Surface Disorders: Short-Term Results. *Eye Contact Lens*. 2013; 39:341-347

Previous studies have also shown that topical amniotic membrane extract (AME) has comparable effect to AMT in promoting epithelialization, decreasing inflammation, and suppressing corneal neovascularization.[5] However amniotic membrane extract lacks the physical characteristics of a bandage and as such it cannot be used as a patch graft.[6] Another previous approach to the use of amniotic proteins to treat ocular disease and injury is the application of amniotic fluid topically delivered to the eye.[7]

[5] Liang L, Li W, Ling S, Sheha H, Qiu W, Li C, Liu Z, Amniotic membrane extraction solution for ocular chemical burns. *Clin Experiment Ophthalmol*. 2009 December; 37(9):855-63.
[6] Sheha H, Liang L, Hashem H, Ramzy M, ZaKi A, Amniotic Membrane Extract for Acute Ocular Chemical Burns, *Techniques in Ophthahnology* 2010 December; 8 (4) pp 146-150
[7] US 2008/0286378 A1.

However, surgically performed AMT renders a relatively high cost and potentially unnecessary surgical trauma and complications. Amniotic membrane retained by a ring does not require surgery, but it is obtrusive, not well tolerated and as a result it suffers from sub-optimal therapeutic outcomes. Amniotic membrane extract—though it shares the healing qualities of intact amniotic membrane—does not have the physical characteristics of a patch. There is, therefore, an unmet need for improved delivery of amniotic proteins for ocular indications.

SUMMARY OF THE INVENTION

The invention described herein is a method and medical device for the treatment of diseases and injuries to the cornea of an eye, that may include a self-retaining patch that incorporates amniotic membrane preparations that is applied using non-surgical means, does not require external mechanical support, is well tolerated by patients, and lasts for a controlled period of time to achieve the ultimate goal of using amniotic membrane preparation in treating ocular surface disorders.

In an embodiment, the invention disclosed herein may be a multi-purpose ophthalmic patch incorporating amniotic extracts and/or placental extracts, mixed with or carried on a biodegradable material. The amniotic patch is formed in the general shape of a contact lens that can easily be placed on the surface of the eye to act as a bandage and protect and enhance the healing of the ocular surface. The inventive patch may achieve the known therapeutic benefits of the amniotic membrane without the need for surgery or a retaining ring to eliminate surgery related complication as well as ring related discomfort. Moreover, the patch is designed with controlled rate of degradation, such that the time it is used for different ocular surface disorders can vary according to the desired treatment period. For instance, if long term treatment is desired, then a lens with a slow degradation rate may be utilized, whereas, if more short term treatment is desired a lens having a faster degradation rate may be utilized.

In an embodiment, the inventive lens-shaped patch includes a clear central section comprising a hydrogel or silicone hydrogel polymer, and a peripheral section comprising a biodegradable carrier material and an active ingredient comprising an amniotic extract and/or placental extract, wherein the biodegradable material and active ingredients are combined, and wherein the central section and the peripheral section are formed into the shape of a contact lens that is applied to a patient's eye. In an embodiment, the clear central section is refractory.

In an embodiment, a method is provided of treating an ocular disease or injury in a patient having an ocular disease or injury, by providing a lens-shaped patch formed of biodegradable carrier material and an active ingredient comprising an amniotic extract and/or placental extract, the lens-shaped patch having a substantially convex exterior surface and a substantially concave interior surface; applying the lens-shaped patch to the patient's cornea, whereby the interior surface of the lens-shaped patch contacts the cornea; and allowing the lens-shaped patch to dissolve while on the patient's cornea.

In an embodiment, a method is provided of treating an ocular disease or injury in a patient having an ocular disease or injury, by providing a lens-shaped patch formed of biodegradable carrier material and an active ingredient comprising an amniotic extract and/or placental extract, the lens-shaped patch having a substantially convex exterior surface and a substantially concave interior surface, wherein the lens-shaped patch has a controlled degradation time; determining a treatment time, according the nature of the ocular disease or injury, during which the lens-shaped patch should be applied to the patient's cornea; selecting the lens-shaped patch that has a degradation rate such that the patch applies active ingredient to the cornea for a time that is equal to or greater than treatment time; and applying the lens-shaped patch to the patient's cornea, whereby the interior surface of the lens-shaped patch contacts the cornea.

In an embodiment, a lens-shaped patch is provided for the treatment of diseases and injuries to the cornea of an eye, where the patch is has a biodegradable carrier material and an active ingredient comprising an amniotic extract and/or placental extract, and the biodegradable material and amniotic and/or placental extract are combined and formed into the shape of a contact lens, such that the active ingredient in the lens-shaped patch is in physical contact with the outer surface of the cornea.

DETAILED DESCRIPTION OF THE INVENTION

The term "amniotic extract" herein means any of various preparations derived from amniotic membrane materials, including preparations derived from amniotic membrane, amniotic stroma and amniotic jelly (e.g. membrane particles obtained or purified via a suitable extraction/purification process such as pulverization or homogenization). Placental extracts of any of various sources may be used in different embodiments of this invention. Placenta extract or placenta membrane may be derived from any of various mammalian sources, including human, sheep, or bovine. Sheep placental extract is available commercially. For many uses, human placental extract may be less antigenic for use in humans. The term "placental extract" herein means any of various preparations derived from mammalian, including human, placenta (e.g. placental particles obtained or purified via a suitable extraction/purification process such as pulverization or homogenization). In this invention, amniotic extracts or placental extracts may be used alone or they may be blended. Any of amniotic extract or placental extract, or blend thereof, may be alternatively referred to as the "active ingredient" herein.

In an embodiment of this invention, the active ingredients are supported by or associated with a biodegradable carrier, filler or matrix. The biodegradable carrier active ingredient is formable into various shapes and configurations according to different embodiments of the invention. In an embodiment of the invention, the biodegradable carrier is formed into substantially the shape and size of a conventional contact lens. A patch formed by combining active ingredients with a synthetic or natural biodegradable and casting the same into the general shape of a conventional contact lens may be referred to as a "lens-shaped patch" or "patch" or "lens patch" herein.

In an embodiment, a lens shaped patch for treating diseases and injuries to the cornea is provided, including a biodegradable carrier material and an active ingredient comprising an amniotic extract and/or placental extract, wherein the biodegradable material and amniotic and/or placental extract are combined and formed into the general shape of a contact lens.

In an embodiment, the base curvature of the lens-shaped patch is similar to or slightly greater than the curvature of the cornea. As such, the inner surface of the patch substantially conforms to the external surface of the cornea and it adheres thereto allowing the patch to remain centered on the cornea.

Figure 1:
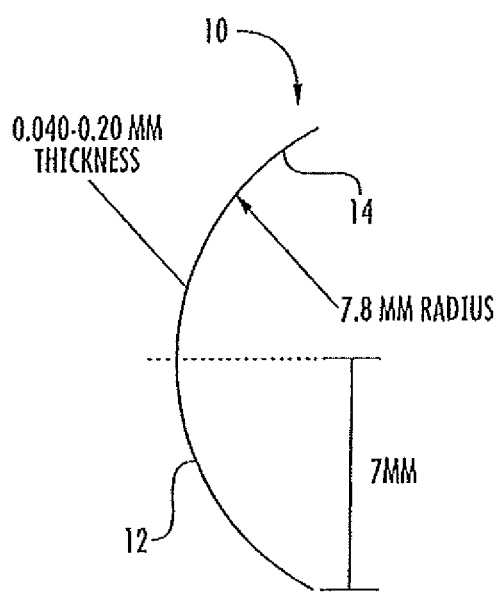
FIG. 1 is a side cross-sectional schematic view of a contact lens-shaped patch according to an embodiment of the invention.
Figure 2:
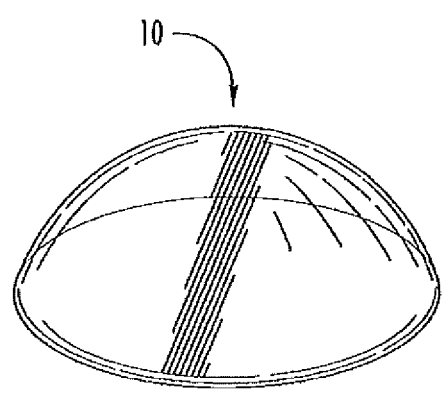
FIG. 2 is a prospective side view of a contact lens-shaped patch according to an embodiment of the invention.
Figure 3:
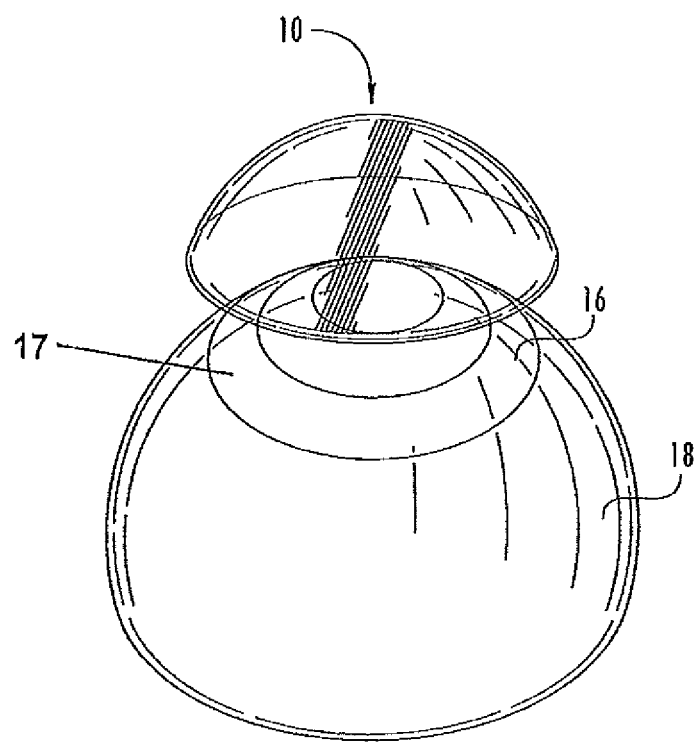
FIG. 3 is a side perspective view of a contact lens-shaped patch positioned for insertion on an ocular surface according to an embodiment of the invention.

In an embodiment of the invention, the inventive lens-shaped patch has a variable thickness and provides no magnification power or vision corrective properties. For example, the patch may have a thickness ranging between 0.040 mm and 0.20 mm and more preferably between 0.04 mm and 0.08 mm. In an embodiment, the lens is approximately 0.05 mm thick. The lens-shaped patch may be made in any of various diameters, preferably in the range of 14-24 mm. In order to conform to a medium-size cornea, the lens patch diameter is most preferably around 14 mm in diameter. The lens patch radius of curvature is within the range of 7.5-9 mm and most preferably a 7.8 mm radius of curvature. For example, FIG. 1 shows a side cross-sectional view of a lens-shaped patch having a diameter of 14 mm and a 7.8 mm radius of curvature. Lens-shaped patch 10 has a substantially convex outer surface 12 and a substantially concave interior surface 14. FIG. 2 shows a perspective view of the lens-shaped patch embodied in FIG. 1. FIG. 3 shows a lens-shaped patch 10 positioned to be inserted over the iris 16 of an eye 18, so that the lens-shaped patch is in physical contact with cornea 17 on the eye. Lens patch 10 is applied with its inner concave surface 14 contacting the cornea. As shown, the lens patch is appropriately sized and shaped to substantially cover the entire surface of the iris 16.

It will be understood by those of ordinary skill in the art that lens patches of other sizes may be molded to fit other eye geometries. In addition, where a numerical range is provided herein for any parameter, it is understood that all numerical subsets of that numerical range, and all the individual integer values contained therein, are provided as part of the invention.

In an embodiment, the inventive lens-shaped patch includes a clear central section comprising a hydrogel or silicone hydrogel polymer, and a peripheral section comprising a biodegradable carrier material and an active ingredient comprising an amniotic extract and/or placental extract, wherein the biodegradable material and active ingredients are combined, and wherein the central section and the peripheral section are formed into the shape of a contact lens that is applied to a patient's eye. In an embodiment, the clear central section is refractory. In this embodiment, the central section has vision corrective properties. In an embodiment, the patch is a contact lens with a peripheral border region comprising an amniotic extract and/or placental extract, which may have utility for soothing eye irritation caused by contact lenses.

Figure 4:
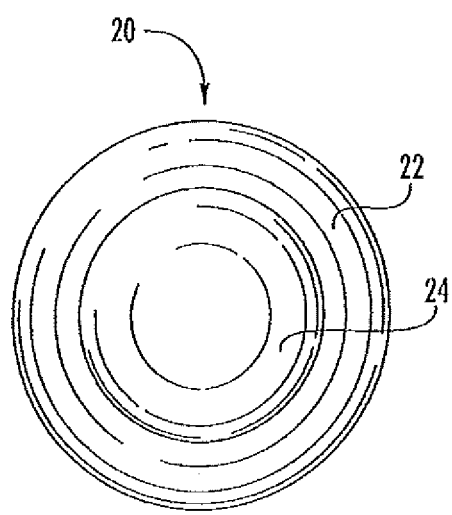
FIG. 4 is a front schematic view of a lens-shaped patch where the biological curative active ingredient is confined to a peripheral ring.

For example, in an embodiment of this invention, a lens-shaped patch may be formed with a hole cut in the center of the lens to increase wearer visibility in that region. Alternatively, a small circular region of PLGA with no placental extract may be placed in the center of the lens to increase wearer visibility. FIG. 4 shows a lens-shaped patch 20 having a two regions, an outer peripheral ring region 22, and an inner central region 24. Outer peripheral ring 22 may contain active ingredients, whereas inner central region 24 may not. In one embodiment, inner central region 24 is a cutout. In another embodiment, inner central region 24 is carrier material (e.g. PLGA) without active ingredients. In either embodiment, the active ingredient is confined to the peripheral band 22.

In an embodiment, the diameter of lens patch 10 is around 14 mm. The diameter of inner central region may be anywhere between 4 mm to 10 mm that allows sufficient light to pass through for reasonable vision.

In use, the lens-shaped patch is applied to a corneal surface like a contact lens and it need not be implanted or supported by external structures like a supporting ring.

In an embodiment, the inventive lens-shaped patch need not be removed. Rather, it may be designed to dissolve in place on a cornea into small bio-acceptable components that may either by absorbed by the body or washed out with the eye's natural processes.

The lens-shaped patch may be translucent or transparent and may be composed of two primary ingredients to create a matrix or similar carrier for carrying curative biological extracts, and provide curative ingredients to an ocular surface. The material used as a carrier or matrix may be any of various natural or synthetic biodegradable materials or blends thereof. For instance, in one embodiment of the invention, a lens-shaped patch is formed of placental extract powder that is embedded in or carried on a poly (DL-lactide co-glycolide) copolymer carrier. The poly (DL-lactide co-glycolide) copolymer provides acts as a biodegradable carrier for the active ingredients. The glycolide carriers provide structural support for shaping the lens-shaped patch.

In an embodiment of the invention, a poly(DL-lactide co-glycolide) copolymer is used as a biodegradable structural carrier material for the lens-shaped patch. Poly(DL-lactide co-glycolide) copolymer is an ester-terminated copolymer of lactide and glycolic acid (PLGA). In an embodiment, the ratio of lactide to glycolic acid is 50:50. Poly(DL-lactide co-glycolide) copolymers (PLGA) with different lactide to glycolide ratios may be used in different embodiments of the invention. Moreover, any of various biodegradable polymers may be used as an alternative to PLGA. For example, poly(DL-lactide-co-caprolactone), methoxy (polyethylene glycol)-b-poly(L-lactide), polylactide, polyglycolide, and other biodegradable polymers known in the art may be used in embodiments of the invention.

PLGA is commercially available, for example, via LACTEL Absorbable Polymers, Birmingham, Ala. PLGA has been used in medical devices, primarily as sutures or cell growth scaffolds. It should be noted that 50:50 PLGA described above provides an excellent balance of the following material qualities: mechanical modulus at 22° C., mechanical modulus at 37° C., <1 month degradation rate at 37° C. in phosphate buffer, optical transparency, high solubility in common organic solvents, and overall material quality.

In addition to, or as an alternative to, synthetic carriers, natural biodegradable carrier materials may be used in different embodiments of the invention. For example, collagen obtained from any of various mammalian sources may be utilized in embodiments of the invention as a biodegradable structural material carrier.

The active ingredients may be bleached and finely ground to render them transparent or translucent. For example, placental extract may be bleached with a suitable solution, such as a solution of approximately 10% aqueous hydrogen peroxide for a period of about 24 hours. Thereafter, the water is removed (e.g. via freeze drying, vacuum drying, air drying), and the resultant placental extract is ground to a powder preferably with a particle size of less than 5 microns, or more preferably a particle size of less than 1.0 microns, or less than 0.1 microns. The degree of transparency or translucency may depend on several factors, including the degree of bleaching of extract powder and the particle size.

Plasticizers and other additives and/or active ingredients may be added in different embodiments of the invention. For example, plasticizers such as triethyl citrate, tributyl acetylacetate, glycerol, or the like may be added.

In an embodiment of the invention, a lens-shaped patch is formed of approximately 90% PLGA by weight and approximately 10% active ingredients by weight. In another preferred embodiment of the invention, the patch is formed of approximately 80% PLGA by weight and approximately 20% active ingredients by weight. Any of various plasticizers may be added in the range of 1-20% by weight.

The following are non-exhaustive possible ranges of respective biodegradable carrier, active ingredient and plasticizer:

10-30% bleached, dried active ingredient, micronized to a particle size of about 5 microns to less than 1.0 microns;
50-90% 50:50 poly(DL-lactide co-glycolide) block copolymer (PLGA) or other biodegradable polymer(s);
0-20% other additives such as plasticizers, other active ingredients, etc.

In other embodiments of the invention, active ingredients may comprise as much as 50% of the lens-shaped patch by weight. In another embodiment, the biodegradable carrier may comprise more than 90% of the lens-shaped patch by weight. The following are non-limiting examples of such ranges:

1-50% bleached, dried active ingredients, micronized to a particle size of about 5 microns to less than 1.0 microns;
20-99% 50:50 poly(DL-lactide co-glycolide) copolymer (PLGA) or other biodegradable polymer(s);
0-30% other additives such as plasticizers, other active ingredients, etc.

In one embodiment of the invention, the constituents of the lens-shaped patch (e.g. biodegradable polymer, active ingredient and any additives) are associated in a matrix or mixture with no covalent bonding or cross-linking of molecules. In this embodiment, the active ingredient is not chemically bound to the carrier material, active ingredient is not chemically bound to active ingredient, and carrier material is not chemically bound to carrier material.

Controlled Biodegradability

Depending on the nature of the ocular condition being treated, the treatment time will vary from a few days to several weeks. These treatment durations are determined by experienced clinicians.

Accordingly, the lens-shaped patches provided herein may be designed to degrade over a specified timeframe. That is, different lens patches may be specifically calibrated to degrade at pre-determined times, ranging from days to several weeks. A specific degradation time may be selected, for example, by varying any of the following: the dissolvable polymer, the ratio of polymer to active ingredient, the plasticizer concentration and type, the thickness of lens patches or a combination of the foregoing. Alternatively or additionally, chemical curing processes may be performed, such as, crosslinking by gamma or e-beam sterilization, or a adding a chemical crosslinker.

The term degradation (or biodegradation) as used herein means the loss of mechanical integrity of the lens-shape patch, followed by the degraded material breaking into small portions that can either be absorbed by the body or slough off the eye in the form of tears.

Figure 5:
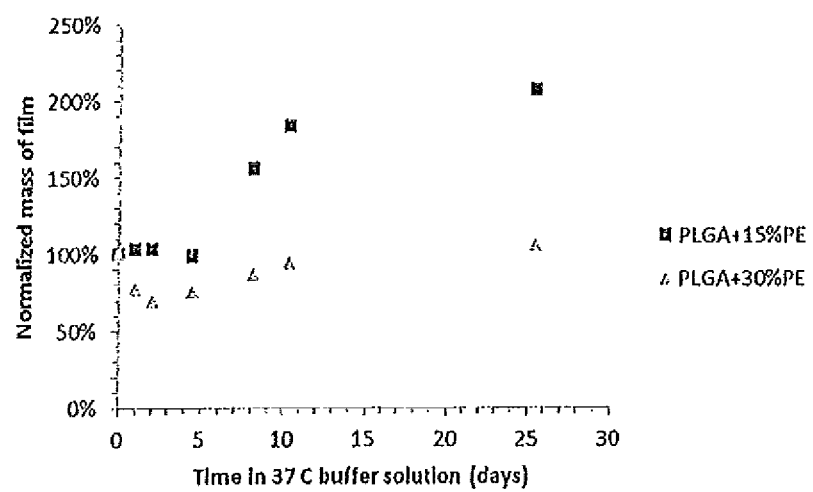
FIG. 5 is a graph of mass changes over time for ~0.1 mm thick lens-patches containing 15% and 30% placental extract, respectively, and 50:50 PLGA.
Figure 6:
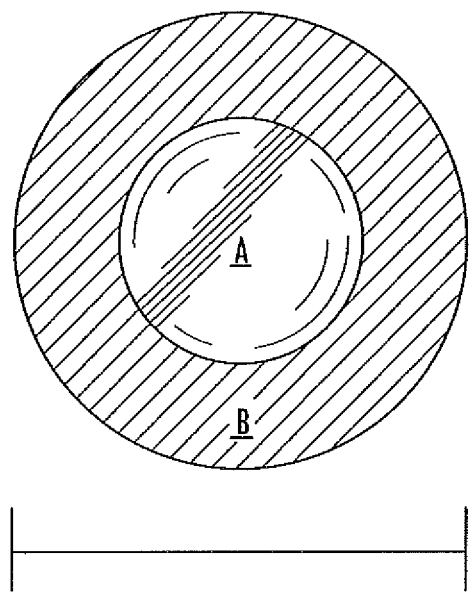
FIG. 6 is a drawing of the patch with a clear central section and a peripheral biodegradable section.
Figure 7:
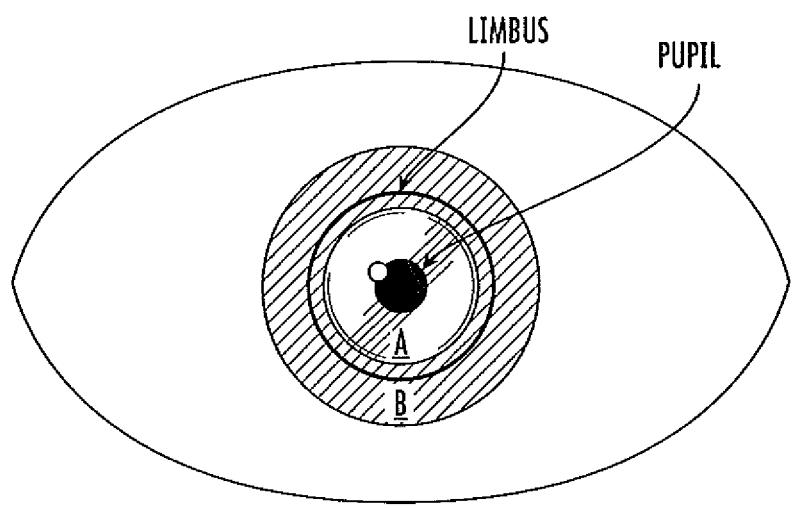
FIG. 7 is a drawing of the patch with a clear central section and a peripheral biodegradable section on the eye of a patient.

It has been demonstrated that in 37° C. phosphate buffer, a PLGA film containing 0-30% sheep placental extract (PE) and having a thickness of ~0.1 mm exhibited significant softening after approximately 18 days. By 25 days, these same films had broken into fragments and with some mechanical action were easily decomposed. Thus, lens patches of ~0.1 mm in thickness should degrade in the eye at ~18-25 days. For example, FIG. 5 shows a graph illustrating mass changes over time for ~0.1 mm thick lens-patches containing 15% and 30% placental extract, respectively, and 50:50 PLGA. As shown, the mass decreases slightly over the first week, as the PE is leached out of the film and into the buffer solution. The mass then increases with time as the PLGA matrix swells with water as part of the degradation process. Note that this behavior may be modified for other mixtures of biodegradable polymer with the extract.

The 50:50 PLGA copolymer is known to degrade faster than other copolymers or homopolymers of lactide and glycolide. Water can diffuse through the matrix, and the PLGA degrades by the action of hydrolysis on the esters in the lactide/glycolide chains. This hydrolysis occurs much faster at 37° C. than at 22° C.

i. Thickness:

With thinner layers of the PLGA-based films, the overall degradation rate should be slightly faster since there is more surface area exposed to the 37 degrees C. water and because mechanical failure (tearing through the thickness) will occur more quickly. However, degradation does not necessarily scale 1:1 with thickness because water can saturate into the PLGA within hours of exposure. As stated, the biodegradation rate of a 0.1 mm PLGA patch lens is approximately 18-25 days. A lens patch of approximately 0.05 mm thickness will degrade in approximately 14-21 days. Thus, extending or reducing the degradation period may be achieved by respectively increasing or decreasing the patch lens thickness.

ii. Active Ingredient Content:

Control of degradation rates may also be effected by altering the concentration of active ingredients. For example, in a lens-shaped patch where amniotic and/or placental extract contents are below ~40% by weight (~40% by volume), most active ingredient particles will be dispersed and isolated within the PLGA matrix. In this situation, the degradation rate will be slightly decreased as the active ingredient level goes from 0-40%, since the dissolution of active ingredients into the surrounding water-based region will lead to cavities in the PLGA matrix which will slightly increase degradation rates. However, this acceleration in degradation rate will be small, since the PLGA matrix will remain continuous.

For active ingredient contents above ~50% by weight (~50% by volume), the active ingredient particles will start to bridge the PLGA matrix, and dissolution of the PE particles will lead to the PLGA matrix to rapidly break down. It may be expected that if 50% or greater PB particles are added, degradation rates of the PE-PLGA film will be very fast, on the order of <1 week.

iii. Plasticizer Content:

Yet another method mechanism of altering degradation rates is through the use of plasticizers. That is, when plasticizers such as triethyl citrate, tributyl acetylacetate, glycerol, etc. are added to the PLGA/active ingredient matrix, the degradation could be significantly accelerated. For example, the 50:50 PLGA has a glass transition temperature of ~45-50° C. [LACTEL product literature], which is still above the 37° C. use temperature. Addition of a plasticizer will suppress the glass transition temperature to close to or below 37° C., leading to the PLGA being significantly softened and a much faster degradation time. With plasticizer at 1-20% by weight, a 0.1 mm thick PLGA film will degrade at 37° C. in phosphate buffer in 1-7 days. Thus, adding varying concentrations of plasticizers will accordingly allow for producing lens patches of varying degradation rates.

iv. Crosslinking

Many biomedical polymers are sterilized with gamma radiation or e-beam sterilization techniques. In addition to preventing future microbial or viral growth, this sterilization has the effect of partially crosslinking the polymer. This method may be used on the PLGA/active ingredient matrix described herein in order to decrease the rate of degradation. That is, crosslinking by gamma or e-beam will make the PLGA material more resistant to degradation and, as such, it may be extend the degradation time by up to 2-3 times depending on the total radiation level imposed by the gamma radiation or e-beam exposure. However, the dosage of gamma radiation or e-beam used for this purpose must be adjusted to maintain the biological activity of the active ingredients.

Additionally or alternatively, a chemical crosslinker could be used in a similar fashion. There are many biologically compatible, bi- and tri-functional chemical crosslinkers that are commercially available. These may include organic molecules terminated with azides, amines, bromides, maleimides, isocyanates, sulfides, and esters.

It will be understood by those of ordinary skill in the art that other additives and active ingredients may be used in different embodiments of the invention. For example, bioactive ingredients (pharmaceuticals or natural ingredients) that are known in the art to assist with healing and limit irritation may be included in addition to the placental or amniotic active ingredients. Biocompatible dyes may also be added to increase the visibility of the lens when being handled, prior to insertion in the eye. Finally, other biocompatible polymers that have a different biodegradation rate than the primary biocompatible polymer may be added.

In one embodiment of the invention, placental extract is encapsulated in biodegradable polymer microcapsules (made of similar biodegradable polymer as discussed above), and then incorporated into an alternate polymer matrix. For example, these microcapsules could be placed hi a traditional contact lens hydrogel and the release of placental extract would be dependent on biodegradation of the microcapsule walls, rather than biodegradation of the full bandage lens.

It will be understood that the patch lens may be formed of different thicknesses and/or geometries in different embodiments of the invention. For example, lenses may be between 0.02 mm and 0.2 mm thick.

In some embodiments of the invention, the lens may incorporate varying thickness to provide a magnification power. Additionally, the lens radius of curvature may be changed to provide more or less centering force on the underlying cornea. The lens diameter may also be varied to fit different corneal sizes or to cover more of the sclera.

The inventive lens-shaped patches may be used to maintain the ocular surface health and to promote healing after injury due to inflammation, infection, trauma or surgery. Because the patch contains naturally active ingredients, and it degrades into bio-absorbable molecules, it is an ideal alternative to bandage contact lenses for protecting the eye.

Inventive lens-shaped patches also may be designed as a drug delivery system. For example, the lens patch may be impregnated or otherwise provided with drugs such as antibiotics, vitamins or other medicines that are to be applied to the eye. The drugs, as such, are delivered directly to a site where they are needed. As mentioned above, the timing of drug delivery may be manipulated by choosing a patch having a desired degradation rate.

Therapeutic Utility

The amniotic extract and placental extracts employed in this invention reduce inflammation, reduce fibrovascular ingrowth, and facilitate epithelialization. These activities will have a healing effect for diseases and injuries to the cornea. This invention provides a method of treating an ocular condition, including providing a lens-shaped patch formed of biodegradable carrier material and an active ingredient comprising an amniotic extract and/or placental extract, where the lens-shaped patch has a substantially convex exterior surface and a substantially concave interior surface. The lens-shaped patch is applied to a patient's cornea, so that the interior surface of the lens-shaped patch contacts the cornea. The lens-shaped patch may be allowed to dissolve while on the patient's cornea.

The inventive lens-shaped patch may be used to therapeutically treat damaged or diseased cornea, limbus and surrounding conjunctiva, in addition to other wounds and conditions. For example, the patch may be used to promote healing after injury due to inflammation, infection, trauma or surgery and/or to treat dry eye or other ocular conditions. Any treatment and/or benefit imparted to a patient's cornea, limbus and/or surrounding conjunctiva is alternatively termed "treatment of an ocular condition" herein.

The following are non-limiting examples of methods of ocular treatment using the inventive lens-shaped patch:

1) Treatment of Dry Eye Syndrome

The inventive lens-shaped patch may be inserted into a patient's eye to treat ocular surface disorders associated with dry eye condition. With the patch so fitted in the eye, it will provide protection and enhance healing of ocular surface. Depending on the desired treatment duration, the patch will dissolve over time and eventually liquefy to provide additional lubrication to the healed ocular surface. The use of the lens-shaped patch may be repeated as needed to protect and maintain ocular surface health. This will provide a sustained level of treatment and may positively impact the quality of life.

2) Treatment of Ocular Surface Trauma Caused by Chemical or Thermal Injury (Burns)

The inventive lens-shaped patch has the potential to enhance healing of the damaged ocular surface. After copious irrigation of the injured surface and removing of any residual chemical particles, the patch will be applied to the ocular surface as a bandage contact lens. Other conventional treatment can be applied while the patch in place. And the size of the patch can be changed depends on the affected surface area. Multiple applications of a rapidly degraded lens can be applied during the acute phase. Slower degrading lens-shaped patches can be used thereafter. As the acute phase of this condition is extremely short, early intervention usually decreases the risk of blindness.

3) Treatment of Non-Healing Conical Ulceration:

The lens-shaped patch may be inserted into a patient's eye to as an adjunct in treating superficial corneal ulcers secondary to trauma, infection, disease of after surgery. Treatment of the underlying cause is recommended, 4) Post-Refractive Treatment:

Postoperative complications after refractive surgery include pain, epithelial defect, and/or haze. The inventive lens patch may present an effective solution to solve these critical problems when inserted post photorefractive keratectomy (PRK).

The inventive method further includes the steps of determining a timeframe required for proper healing and/or treatment of an ocular condition ("heal rate") and selecting a lens-shaped patch that has an expected degradation timeframe (degradation rate) that is the same as or greater than the expected heal rate. Once the determination of a heal rate is made, a clinician inserts a lens patch having a matching degradation rate or a patch having a degradation rate that is greater than the heal rate into the eye of a patient. The patient is then free to go home wearing the patch, which will dissolve on its own, potential averting the need to return to the doctor for removal, and also dispensing with the need for maintaining rings required in prior art systems.

The inventive device and method is also of utility for treating corneal injuries to non-human mammals, including pets and livestock. For example, the method can be used to treat ocular injuries in dogs, cats, horses, cattle, sheep, pigs, etc.

Example

In embodiments of the invention, the inventive lens patches are formed as described below.

i. Sheep Placental Extract Lens-Shaped Patch

PLGA is dissolved in a suitable solvent (e.g. a blend of 95% acetone and 5% N,N-dimethylacetamide), and bleached sheep PE (20% by weight compared to the PLOA) is added to this mixture and it is wet ball milled until the mixture is transparent. This mixture is then cast onto a smooth, low energy surface (e.g., Teflon-coated glass) to produce a film of PLGA+PE with a dry film thickness of 0.040-0.050 mm. The film is then carefully dried, first under room temperature air, and then under vacuum, until it is stiff and durable. The film is then thermoformed at 70° C. into the bandage lens-shaped patch and demolded at 0° C. A concave or convex thermoforming mold may be used. After thermoforming, the bandage lens is trimmed or punched to the appropriate diameter. This solvent casting and molding process leads to a highly uniform, high optical transparency product.

In another embodiment, patch lenses may be produced by compounding the PB powder and PLGA at elevated temperatures, followed by hot pressing sheets, and finally, followed by thermoforming to lens shapes. Alternatively, extract powder and PLGA are compounded at elevated temperatures, followed by compression molding to lens shapes. In another alternative, extract powder and PLGA are injection molded at elevated temperatures into a lens cavity.

The invention claimed is:

1. A lens-shaped patch for the treatment of diseases and injuries to the cornea of an eye, comprising
    a. a clear central section comprising a hydrogel or silicone hydrogel polymer, and
    b. a peripheral section comprising a biodegradable carrier material and an active ingredient comprising an amniotic extract and/or placental extract, wherein the biodegradable material and active ingredients are combined to form a uniformly blended peripheral section, and
    c. wherein the central section and the peripheral section are formed into the shape of a contact lens that is applied to a patient's eye.

2. The lens-shaped patch of claim 1, wherein the clear central section is refractory.

3. The lens-shaped patch of claim 1, wherein the biodegradable carrier material in the peripheral section comprises collagen from a mammalian source.

4. The lens-shaped patch of claim 1, wherein the biodegradable carrier material in the peripheral section comprises a poly (DL-lactide co-glycolide) copolymer.

5. The lens-shaped patch of claim 1, wherein the ocular disease or injury is any of: dry eye syndrome, corneal trauma, corneal inflammation, corneal thermal injury, or corneal ulcers.

6. The lens-shaped patch of claim 1, wherein the clear central section has no refractive power.

* * * * *